(12) United States Patent
Weil et al.

(10) Patent No.: US 7,567,837 B2
(45) Date of Patent: *Jul. 28, 2009

(54) ENHANCED RHYTHM IDENTIFICATION IN COMPRESSION CORRUPTED ECG

(75) Inventors: Max Harry Weil, Rancho Mirage, CA (US); Joe Bisera, Camarillo, CA (US); Yongqin Li, Palm Springs, CA (US)

(73) Assignee: Institute of Critical Care Medicine, Rancho Mirage, CA (US)

( * ) Notice: Subject to any disclaimer, the term of this patent is extended or adjusted under 35 U.S.C. 154(b) by 177 days.

This patent is subject to a terminal disclaimer.

(21) Appl. No.: 11/367,685

(22) Filed: Mar. 3, 2006

(65) Prior Publication Data

US 2006/0149157 A1 Jul. 6, 2006

Related U.S. Application Data

(63) Continuation-in-part of application No. 10/741,302, filed on Dec. 19, 2003, now Pat. No. 7,039,457.

(51) Int. Cl.
*A61N 1/39* (2006.01)
(52) U.S. Cl. ............................................. 607/6; 607/5
(58) Field of Classification Search .................. 128/901; 607/3–6; 600/513, 518
See application file for complete search history.

(56) References Cited

U.S. PATENT DOCUMENTS

| | | | |
|---|---|---|---|
| 5,029,082 A | | 7/1991 | Shen et al. |
| 5,417,221 A | * | 5/1995 | Sickler ........................ 600/509 |
| 6,287,328 B1 | * | 9/2001 | Snyder et al. ................ 600/509 |
| 6,360,125 B1 | | 3/2002 | Weil et al. |
| 6,390,996 B1 | * | 5/2002 | Halperin et al. ............... 601/41 |
| 6,393,316 B1 | | 5/2002 | Gillberg et al. |
| 6,961,612 B2 | * | 11/2005 | Elghazzawi et al. ............. 607/6 |
| 2004/0162585 A1 | | 8/2004 | Elghazzawi et al. |

* cited by examiner

*Primary Examiner*—George R Evanisko
*Assistant Examiner*—Amanda Patton
(74) *Attorney, Agent, or Firm*—Leon D. Rosen

(57) ABSTRACT

A method is provided for analyzing the condition of a patient to determine whether or not a defibrillation shock should be applied, without stopping CPR (primarily chest compressions). While chest compressions continue to be applied to the victim, the system differentiates between (1) a perfusing rhythm that has the capability of leading to a beating heart without a shock and (2) ventricular fibrillation (VF) which sometimes occurs in the presence of ventricular tachycardia (VT), in which there is no capability for leading to a beating heart without a shock. Defibrillation shocks should be applied only when needed and that is in the presence of VF and sometimes in the presence of VT. Electrocardiographic (ECG or EKG) signals obtained from electrodes applied to the patient's chest are analyzed so that the presence of a QRS signal characteristic of a rhythm which has the potential of supporting a beating heart, or the absence of a QRS signal which indicates ventricular fibrillation, may be detected in the presence of artifacts resulting from chest compressions.

3 Claims, 8 Drawing Sheets

ECG OF QRS COMPLEX CORRUPTED BY COMPRESSION ARTIFACTS

ECG OF VF CORRUPTED BY COMPRESSION ARTIFACTS

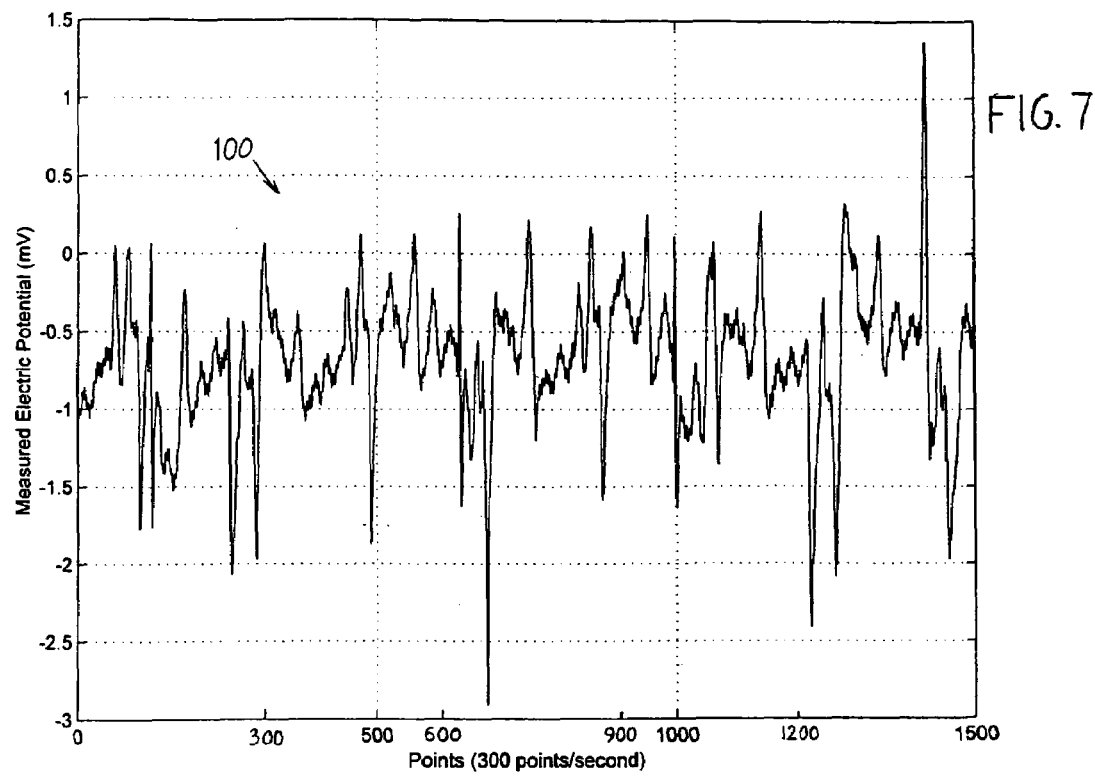
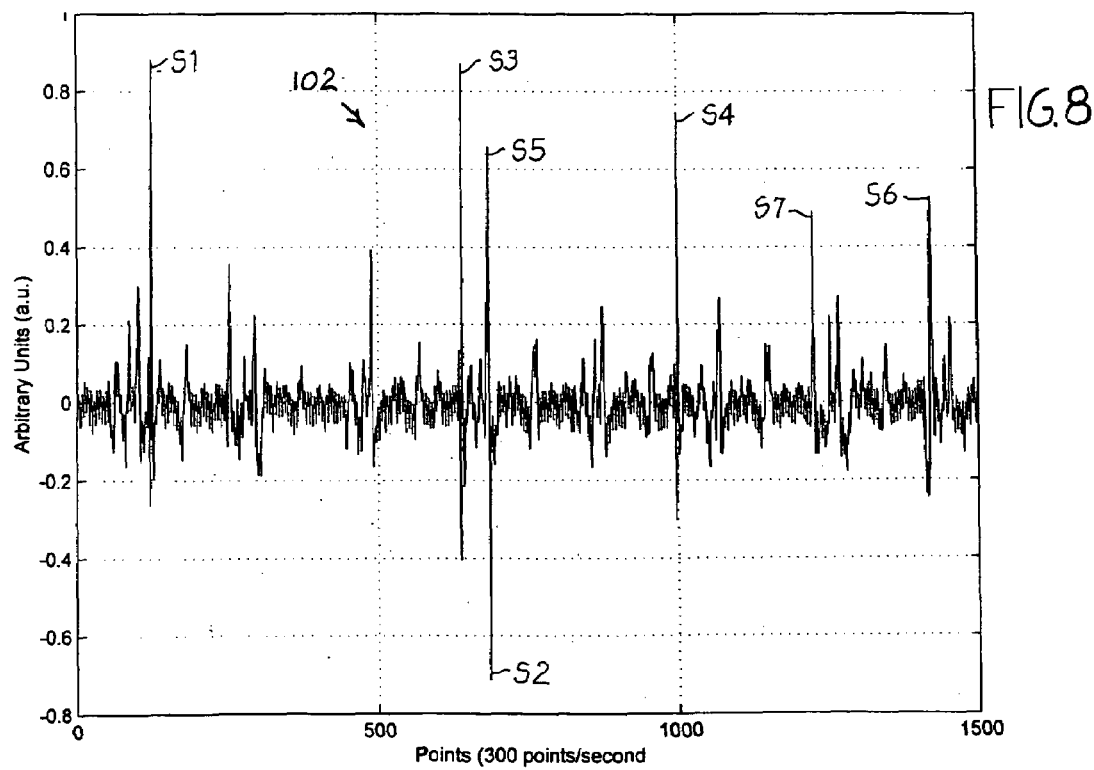

ENHANCED RHYTHM IDENTIFICATION IN COMPRESSION CORRUPTED ECG

CROSS-REFERENCE

This is a continuation-in-part of U.S. patent application Ser. No. 10/741,302 filed Dec. 19, 2003, now U.S. Pat. No. 7,039,457.

BACKGROUND OF THE INVENTION

Electrical shocks are harmful to a heart attack victim, although they are necessary for survival if the victim's heart is in a state of ventricular fibrillation (VF). Electrical shocks that are delivered to a heart that has a weak but detectable beat (which produces QRS signals) harm the patient by interfering with the capability to pump blood and by damaging the heart muscle. U.S. Pat. No. 6,393,316 describes a method for determining whether or not to apply a defibrillating shock.

If other people are present at the onset of a heart attack and especially when loss of consciousness occurs, bystander CPR (cardiopulmonary resuscitation) greatly increase the chance of survival. Basic to CPR is the initiation and continuation of chest compressions, and sometimes also the interval delivery of breaths into the victim's mouth or nose. ECG (electrocardiograhpic) signals generated by electrodes attached to the victim's chest, can be used to determine whether or not to apply a defibrillation shock to the patient, to reverse ventricular fibrillation. Currently, this requires the rescuer to stop chest compression and to "stand back" away from the patient for many seconds to preclude shocking the rescuer and to stop adding chest compression artifacts to the ECG signals so a "clean" ECG signal can be analyzed. This interruption of chest compressions adversely affects the survival possibility of the victim.

Chest compressions produce additional signal components that represent artifacts on the victim's ECG signals that are transmitted through electrodes applied to the patient's chest. Such artifacts due to chest compressions are typically of much greater amplitude than the actual ECG signals of the victim when the chest is not compressed. As a result, portions of an ECG signal arising from the heart are masked by the artifacts. This could preclude accurate analysis of the patient's condition and a decision to apply a defibrillation shock.

Conventional automatic external defibrillators, which automatically analyze the ECG and generate defibrillation shocks, avoid this problem by instructing the rescuer to leave the victim untouched for as long as perhaps 25 seconds so the ECG signals from the victim are not corrupted to facilitate their analysis. The problem with this approach is that the suspension of chest compressions reduces circulation of blood in the victim's body and therefore compromises survival. An alternative is to shorten the interval of "step back, don't touch the patient". A protective sheet, described in U.S. Pat. No. 6,360,125, can be placed over the victim's chest to avoid transmitting a shock to the rescuer so as to reduce the "step back, don't touch" interval to slightly more than required to obtain "quiet" ECG signals to analyze. However, regardless of the length of the "quiet" period during which the ECG is evaluated to determine if the patient's heart is experiencing VF, the chest compressions which maintain circulation are interrupted. Prior studies have demonstrated that the cessation of compressions by as little as 10 seconds reduces the probability of successful defibrillation by as much as 50%.

SUMMARY OF THE INVENTION

In accordance with one embodiment of the present invention, the rescuer continues CPR including chest compressions while the ECG signals from the victim are analyzed by a doctor or other health professional who is caring for the victim, or by an AED (automatic external defibrillator). The ECG signal is evaluated despite the continuing CPR, to determine whether the victim's heart has a perfusing rhythm so a shock should not be applied, or has a rhythm (principally VF) which probably can only be reversed with a defibrillating shock. If a high potential benefit of a defibrillating shock is identified by the intelligence of the AED, the rescuer may be instructed to stand back only during a brief interval of no more than five seconds during which the shock is delivered. As an alternative, the rescuer may continue to apply chest compressions if an insulating blanket protects the rescuer from the shock. In either case, there is no prolonged interruption of chest compression to provide an ECG signal free of chest compression artifacts for analysis.

Applicant analyzes the electrocardiographic signal to differentiate between a "shockable" or "non-shockable" condition, in the presence of large amplitude artifacts produced by chest compressions. Chest compression artifacts and "native" QRS rhythms may occur at almost the same frequency, though the two signals repeatedly move into and out of phase. High amplitude artifacts are followed by short periods during each cycle that are free of such artifacts. When the periods between high amplitude artifacts contain QRS rhythms (which occurs when chest compression artifacts and QRS rhythms are close to 180° out of phase), the QRS rhythms can be detected. If such QRS rhythms are not detected during a significant period of time, then this indicates that the patient is in a state of VF and a defibrillating shock should be applied. A shock should be applied especially if an additional ECG analysis predicts a successful defibrillating shock (as described in U.S. Pat. No. 5,957,856).

The novel features of the invention are set forth with particularity in the appended claims. The invention will be best understood from the following description when read in conjunction with the accompanying drawings.

BRIEF DESCRIPTION OF THE DRAWINGS

FIGS. 7-10 are graphs showing how applicant processes ECG signals from a patient suffering VF (ventricular fibrillation) who is undergoing chest compressions.

DESCRIPTION OF THE PREFERRED EMBODIMENT

Figure 1:
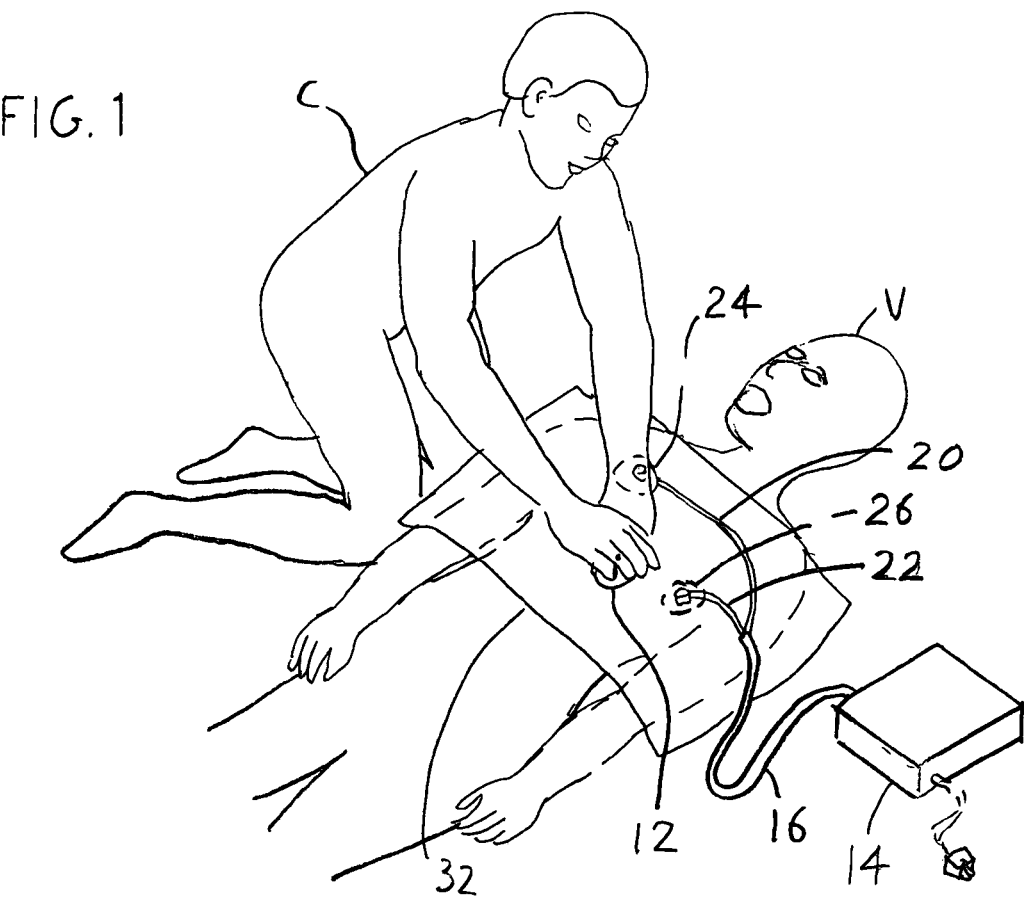
FIG. 1 is an isometric view showing a rescuer performing chest compressions to a victim while an AED (automatic defibrillator) is connected through two electrodes to the victim.

FIG. 1 illustrates a patient or victim V who has signs of cardiac arrest and who is being treated by a rescuer C. The rescuer may be a person who is a bystander and who has taken a CPR course. The rescuer has applied the electrodes of an AED (automatic external defibrillator) 14 that was available at the site of possible cardiac arrest, and is performing chest compressions at the lower chest area 12. An alternative is that a manually controlled defibrillator is connected to the patient and is controlled by a doctor or other health care provider who is analyzing ECG signals of the victim. The automatic defibrillator 14 can apply high-voltage (e.g. 2,800 volts) shocks when the intelligence built into the defibrillator confirms the presence of a rhythm that prompts delivery of an electrical shock. The defibrillator has a cable 16 with wires 20, 22 having conductors that are connected to first and second electrodes 24, 26. The electrodes are attached to the skin of the victim at conventional locations under the right collar bone and left lower chest. The entire ECG is taken without moving the electrodes, so the ECG signals are taken all from the same location on the victim. The rescuer applies downward forces or compressions to the sternum. It is noted that in some cases a rescuer also may blow air into the mouth or nose of the patient by mouth-to-mouth or mouth-to-nose breathing, sometimes using a mask or barrier device. An electrically insulating sheet 32 has been placed between the rescuer and the patient, so the rescuer can continue to apply chest compressions when the defibrillator delivers an electrical shock. As an option, the rescuer may be prompted prior to the delivery of a shock by the AED, and the rescuer may choose to stop chest compressions for a few seconds (generally less than 5 seconds) to allow for the shock to be applied.

Current versions of AED's require a "quiet" period of perhaps 12 to 25 seconds, when chest compressions are suspended and during which the intelligence of the defibrillator determines whether or not a shock is required. During this "quiet" period the computer intelligence applies algorithms to analyze the rhythm in the ECG signal to determine whether the patient has VF, in which case delivery of a shock is triggered. If the victim is producing a rhythm which would be indicative of a potentially beating heart (perfusing rhythm), no shock is delivered and continued CPR is advised. Though current defibrillators may actually require only as little as 7 seconds to identify the presence of a non-shockable rhythm, chest compressions are stopped for a longer period. As mentioned above, such "quiet" periods substantially reduce the success of defibrillation and survival from cardiac arrest. Multiple shocks may be required and therefore several "quiet" periods may occur during which CPR is suspended for periods of time that prejudice restoration of circulation.

Figure 2:
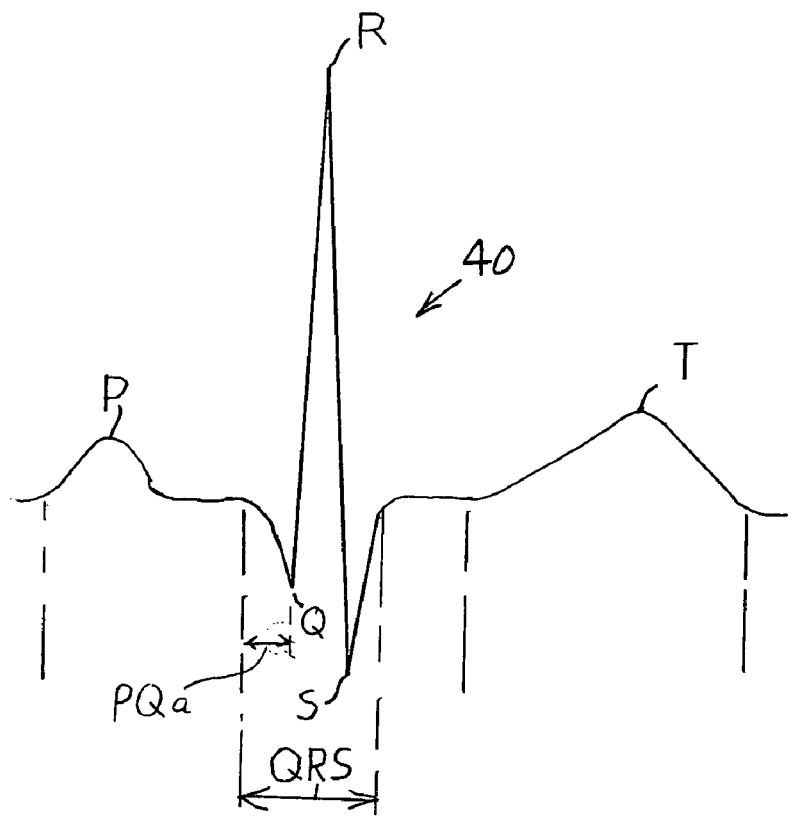
FIG. 2 is a graph showing an ECG signal produced by a healthy beating heart.
Figure 3:
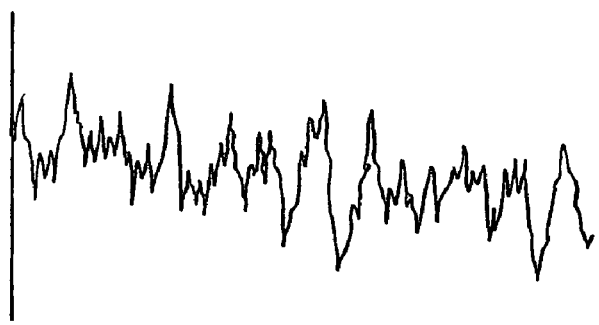
FIG. 3 is a graph showing an ECG signal produced by a heart in a state of VF (ventricular fibrillation).

In accordance with the present invention, the application of chest compressions by the rescuer is not interrupted while the intelligence of the automated defibrillator or a caregiver operating a manual defibrillator, determines whether a defibrillation shock is indicated. FIG. 2 is a graph 40 showing one cycle of an ECG signal obtained from a patient with a healthy heart in perfusing rhythm. The electrical cycle is conventionally identified by the letters characteristic of the beating heart, which are a PQRST complex. The five letters indicate five points along the electrical cycle. The main area of interest is the area QRS, in which there is an electrical "spike". This spike is the part of the ECG cycle which corresponds to the electrical event which triggers the mechanical pumping of the ventricles and which creates the heartbeat and blood flow to the body. FIG. 3 is a graph showing a typical ECG of a heart in VF. The QRS complex is not present, which indicates a quivering heart, which is a heart with VF and which does not produce blood flow and perfusion of the vital organs. The P-Q and S-T parts of the electrical cycle are also absent.

Figure 4:
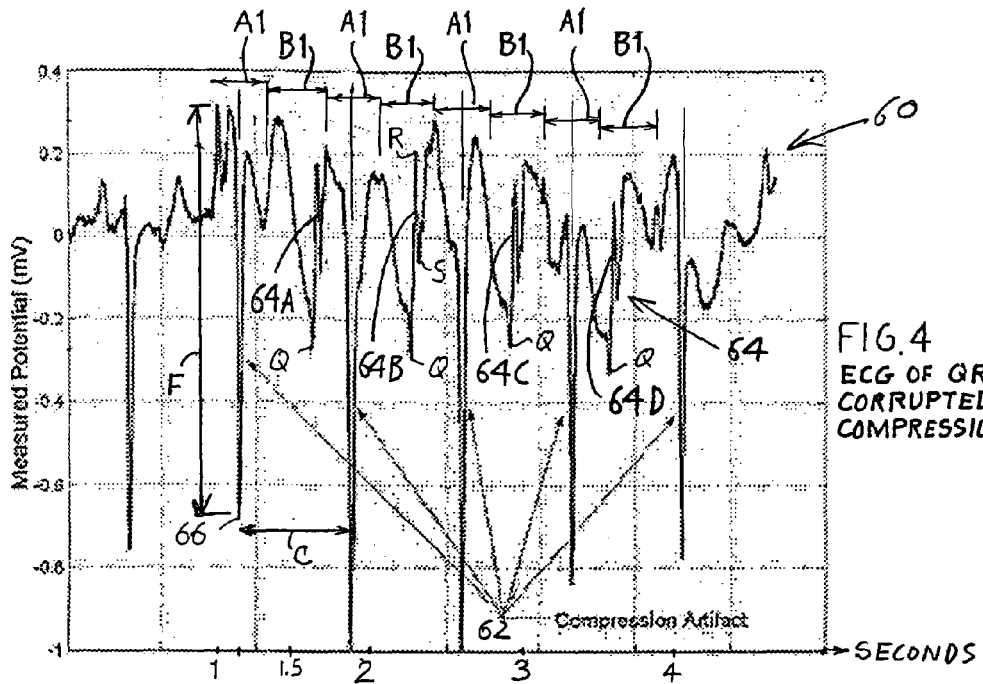
FIG. 4 is a graph showing an ECG signal produced by a healthy beating heart corrupted by artifacts produced by chest compressions of the type applied by the rescuer.

FIG. 4 illustrates an ECG from a patient with a healthy heart generating perfusing rhythms, but in the presence of artifacts due to chest compressions. The graph 60 includes compression artifacts 62 resulting from chest compressions, together with QRS complexes 64, labeled 64A-64D and resulting from the electrical signals of the beating heart. The electrical signal of a healthy heart is typically more regular in the shape of the signal in each cycle and in the time periods of the cycles. In FIG. 4, the chest compression artifacts 62 are also applied regularly although their amplitude varies somewhat. The frequency of the beating heart QRS complexes 64 and the frequency of the chest compressions and corresponding compression artifacts 62 are close, but are never exactly the same. As a result, there is a constant phase shift between the QRS complexes 64 and the compression artifacts 62.

The fact that there is a constant change in phase between the compression artifacts 62 in FIG. 4 and the QRS complexes 64, and the fact that the compression artifacts 62 are of brief duration and high amplitude, allows some of the QRS complexes to be separated out for analysis. In one approach, the ECG signal is modified by deleting all pulses of high amplitude, including the peaks of the large amplitude pulses and perhaps 12.5% of the period on either side of each large pulse peak. Large amplitude peaks may be defined as those of an amplitude exceeding a certain multiple of the average amplitude and having a large derivative (slope), but other criteria can be used. The resulting graph then can be analyzed in a manner similar to analysis of ECG signals which are not corrupted by chest compression artifacts.

Figure 5:
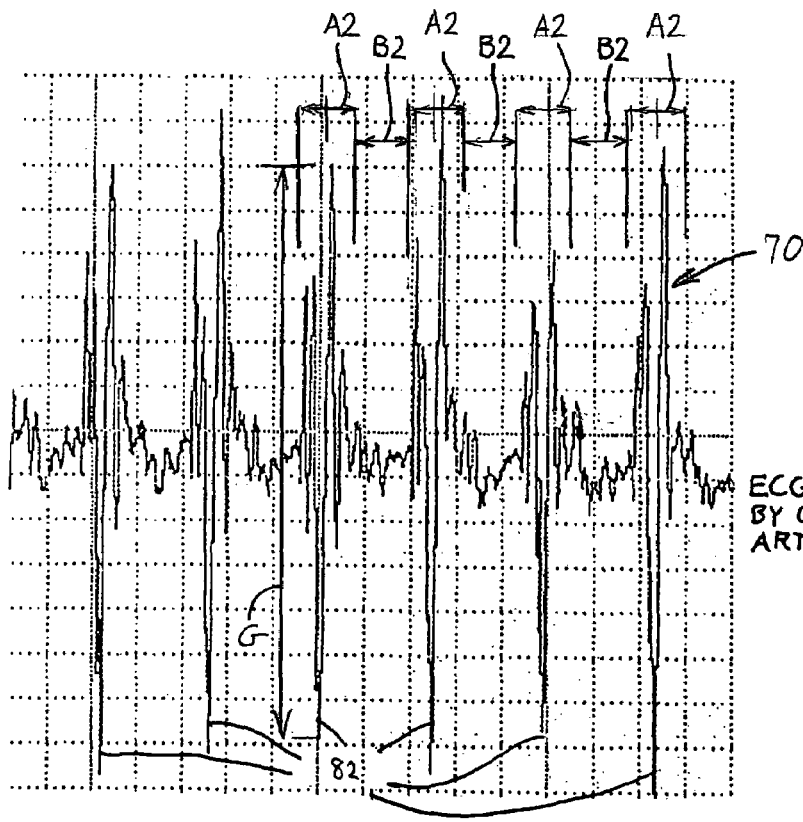
FIG. 5 is a graph showing an ECG signal produced by a heart in a state of VF in the presence of artifacts resulting from chest compressions applied by a rescuer with artifact amplitudes about the same as those shown in FIG. 4.

In another approach, QRS complexes 64 of FIG. 4 lying about halfway between adjacent compression artifacts, such as 64A, 64B, 64C, and 64D, are taken and analyzed. Perhaps four or five of the QRS complexes that lie about halfway between compression complexes (e.g. between 25% and 75% of the time distance between compression artifacts 62) can be added together where points such as the Q's (point of high slope and high slope change, lying in between the artifacts 62) overlap. A single QRS complex such as 64B is cross-correlated with the average of the four or five QRS complexes. In FIG. 4, the time C between the peak signals 66 of the chest compression artifacts are regular, and the periods A1 extending 12.5% before and after each compression artifact peak 66 are excluded from analysis. Only the periods B1 extending from 25% to 75% of the peak compression artifacts are analyzed for the presence of QRS complexes. In FIG. 4, three QRS complexes 64A, 64B, 64C lie completely within the periods B1, FIG. 5 shows an ECG signal 70 from a patient whose heart is undergoing VF while chest compressions of an average amplitude G are being applied. The chest compression artifacts 82 can be removed by one of the processes described above. That is, the only periods analyzed are the periods B2 that extends 12.5% before and after each artifact 82. The ECG signal in periods B2 do not display any QRS complexes. That is, in the graph there are no sharp spikes between the compression artifacts, which indicates the presence of the bizarre VF condition characterized by the absence of QRS. This triggers delivery of a defibrillating shock. A large number (e.g. 60 consecutive B2 periods) of signals in periods B2 are analyzed to try to detect QRS complexes, to be sure that all QRS complexes do not happen to lie in the periods A2 of chest compressions.

The periods B1 and B2 in FIGS. 4 and 5 are analyzed to determine whether or not a group of ECG signals of periods B1 or B2 are of the same shape and/or have the shape of a QRS complex. One way is take the signals portions of durations B1 at 64A, 64B, 64C in FIG. 4 and compare them.

When comparing signals of duration B1 at 64A-64C, the absolute value of each signal is taken. The absolute value is autocorrelated to emphasize large amplitude change such as near the points Q. Then, pairs of signal portions of durations B1 at 64A-64C are cross-correlated. This involves multiplying corresponding points along the two signals to obtain a cross-correlation signal followed by determining the area under the cross-correlation signal. After the area is obtained, only one signal is shifted slightly and a new cross-correlation signal is obtained. This is repeated until the cross-correlation signal whose area is greatest is obtained. Such cross-correlation numbers are obtained for a plurality of pairs of signals.

In FIG. 4, pairs of signals 64A, 64B, or 64C, 64D are similar, so the sum of the cross-correlation numbers (areas under the best cross-correlation graphs) is high, indicating that all signals (of periods B1) are similar. In FIG. 5, the cross-correlation numbers are low, indicating that all signals (of periods B2) are not similar.

FIGS. 7-14 contain graphs indicating how signals representing VF and QRS in the presence of chest compression artifacts are analyzed by an algorithm that uses crosscorrelation and autocorrelation. FIGS. 7-10 are all for a ECG signal for a case of VF, while FIGS. 11-14 are all for an ECG signal for a case of QRS complexes.

FIG. 7 contains a graph 100 that is a raw ECG signal for a patient with VF, in the presence of chest compression of about the same amplitude as peaks of the VF alone. FIG. 8 is a graph 102 that represents the Wavelet Transform of FIG. 7. The Wavelet Transform is largely similar to the derivative, in that the slopes, but not absolute values, of the signals of FIG. 7 are present in FIG. 8. The Wavelet Transform is also similar to taking the DC (direct current) component out of the AC (alternating current) signal of FIG. 7.

Figure 9:
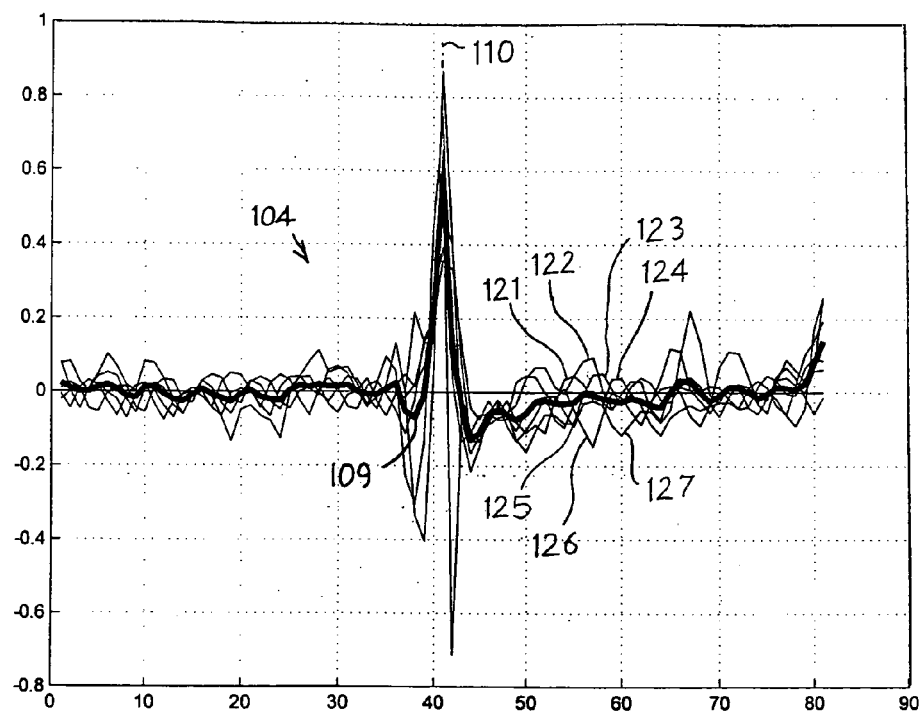

FIG. 9 is a set 104 of graphs obtained by first taking spike regions for the seven largest peaks (e.g. S1 through S7) in FIG. 8. Each spike region includes a peak and the signal extending 0.2 second prior to and 0.2 second after the peak. The peaks of the spike regions are aligned along the horizontal axis so they all lie on a vertical line 110 of FIG. 9. The dark line 109 in FIG. 9 is the average of an amplitude of all of the spike regions of FIG. 9 (other than the dark line itself).

Figure 10:
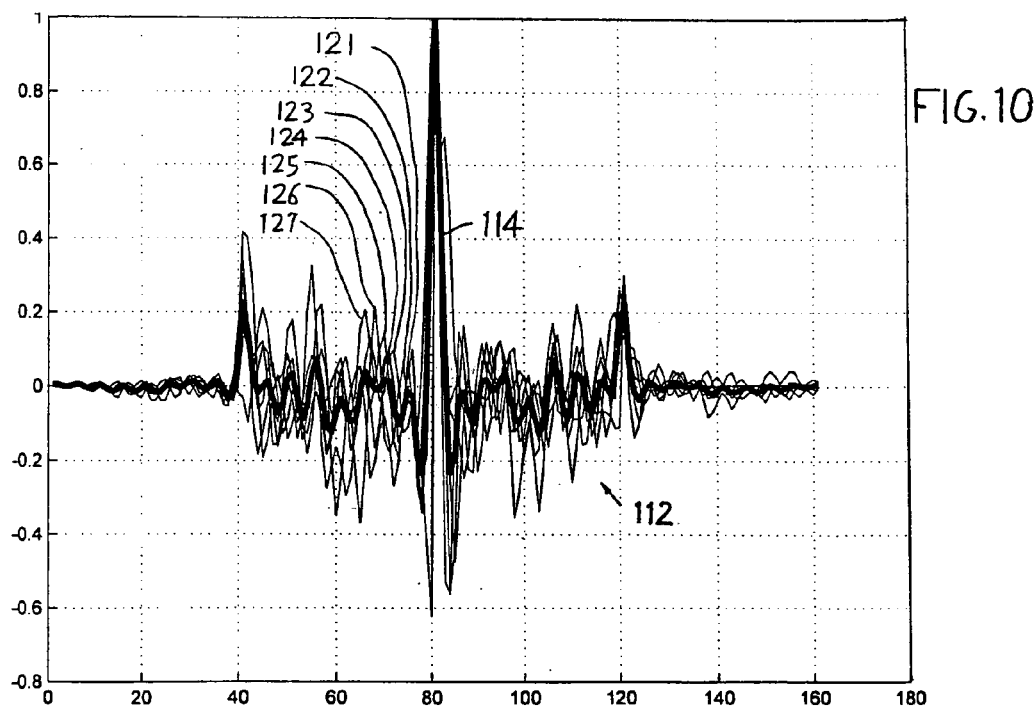

FIG. 10 is a set 112 of graphs obtained by computing the autocorrelation of the seven spike regions of FIG. 9 to obtain dark and thick line 114, and by computing the crosscorrelations of the seven spike areas to obtain the thin lines 121-127. The empty "white" space between the thick line 114 and each of the thin lines 121-127 is calculated. If there is a large white area, this indicates VF for that thin line. If there is a small white area, this indicates a QRS complex for that thin line. The "white" space for a thin line is the integral of the magnitude (absolute value) of the difference between line 114 and one of the thin lines 121-127.

Figure 11:
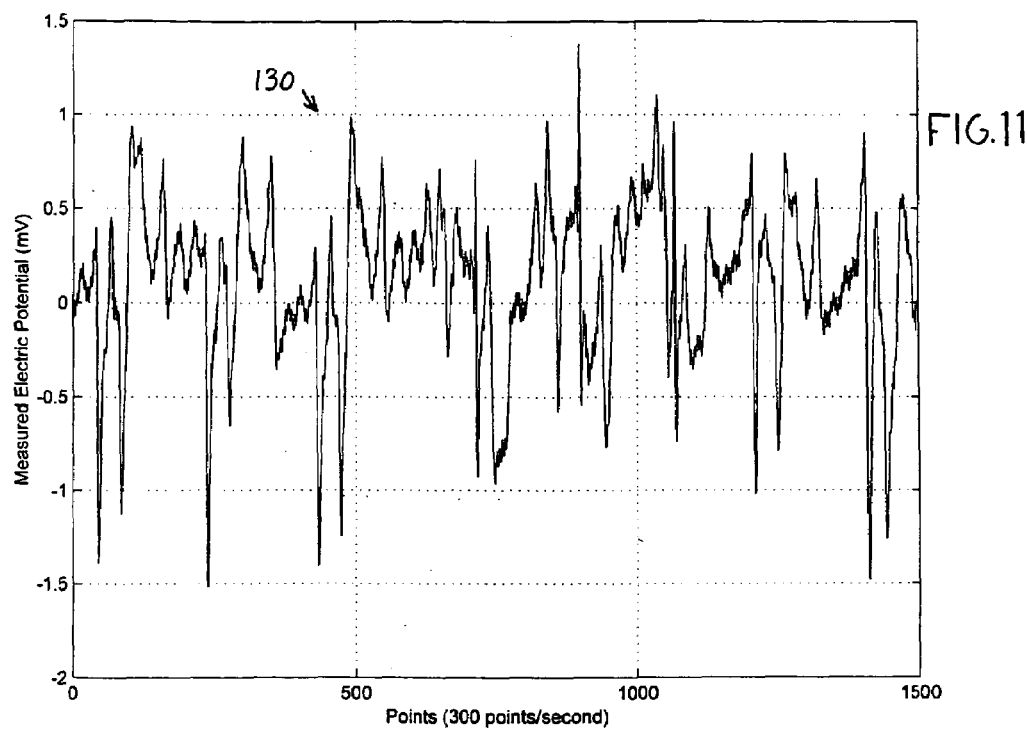
FIGS. 11-14 are graphs corresponding to those of FIGS. 7-10, respectively, but for ECG signals from a patient with a beating heart.
Figure 12:
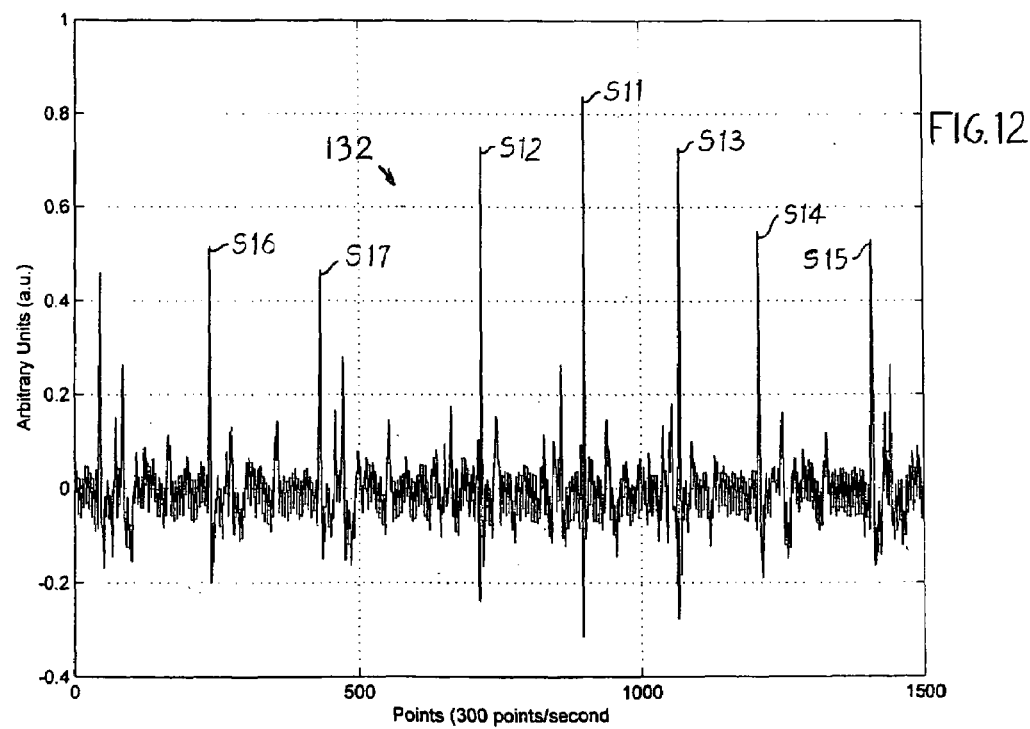
Figure 14:
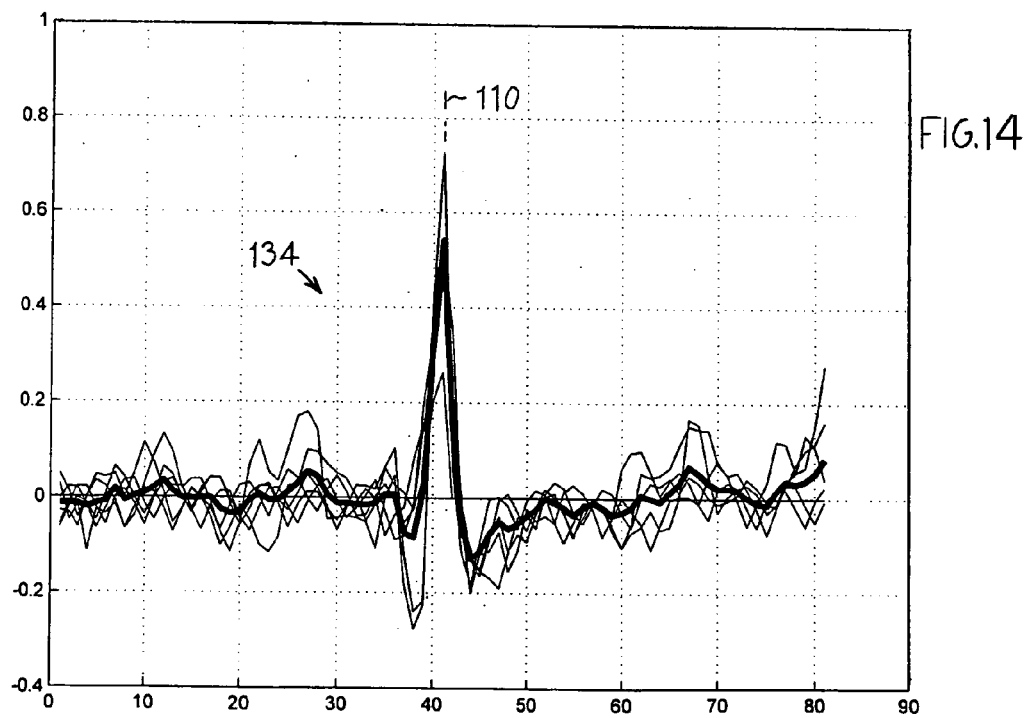

FIG. 11 contains a graph 130 that is a raw ECG signal containing QRS complexes. FIG. 12 is a graph 132 that is a Wavelet Transform of FIG. 11. FIG. 14 includes a set 134 of graphs obtained by following the same process described for FIG. 9. That is, applicant first takes spike regions for the seven largest peaks S11-S17 in FIG. 12. Each spike region includes a peak and the signal portion 0.2 second prior to and following the peak.

Figure 13:
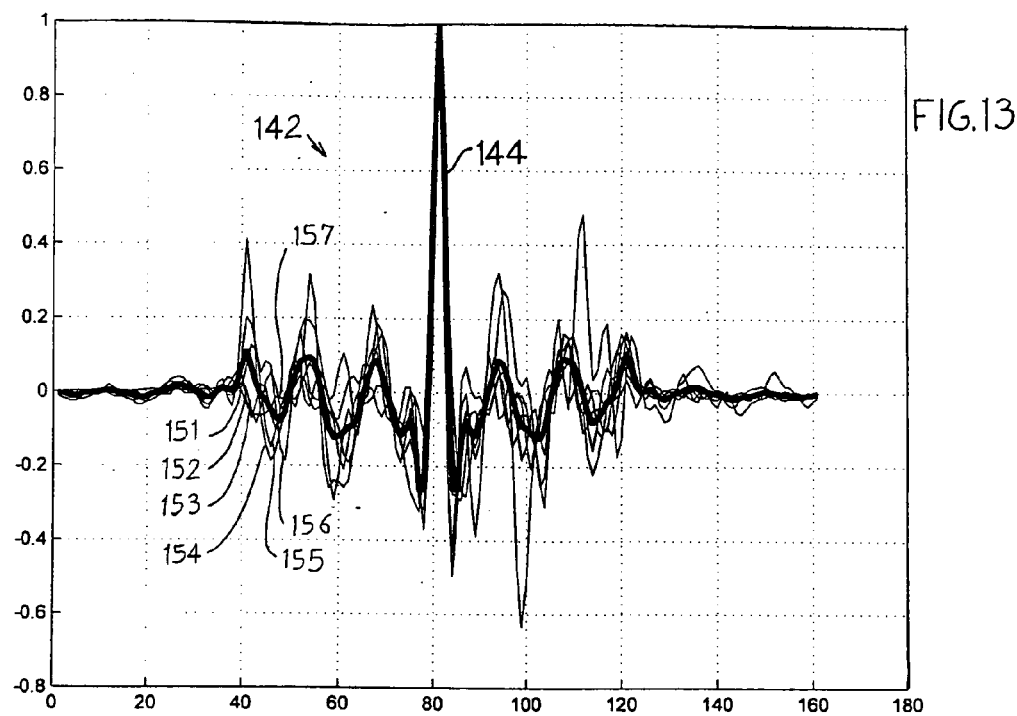

FIG. 13 is a set 142 of graphs obtained by computing the autocorrelation of the seven spike regions of FIG. 12 to obtain dark and thick line 144, and by computing the crosscorrelations of the seven spike areas to obtain the thin lines 151-157. The empty "white" space between the thick line 144 and each of the thin lines 151-157 is calculated, as the integral of the magnitude of the difference between the thick line and each thin line. If a small white area (an integral smaller than a preset amount) has been calculated for a thin line, this indicates a QRS complex, while a large white area (an integral larger than the preset amount) indicates VF for that thin line.

A visual comparison of the crosscorrelations of FIGS. 10 and 13 shows that for the VF set 112 of FIG. 10 the thin lines 121-127 are largely out of phase with the thick line, which results in a large "white" area indicating VF. For the QRS complexes of FIG. 13, the thin lines 151-157 are largely in phase with the thick line, especially near the center 110 of the thick line; this indicates a QRS complex. Actual computing of the "white" area between a thick and thin line in FIGS. 10 and 13 will show this difference.

In applicant's algorithm, if a majority (four of the seven) spike regions have less than the predetermined white area (between themselves and the thick line), then the ECG is deemed to be a genuine QRS rhythm (corrupted by compression artifacts). If a majority (four of seven) spike regions have more than the predetermined white area then the ECG is deemed to represent VF. The white area which is the dividing line can be determined by tests on patients in emergency facilities.

Figure 6:
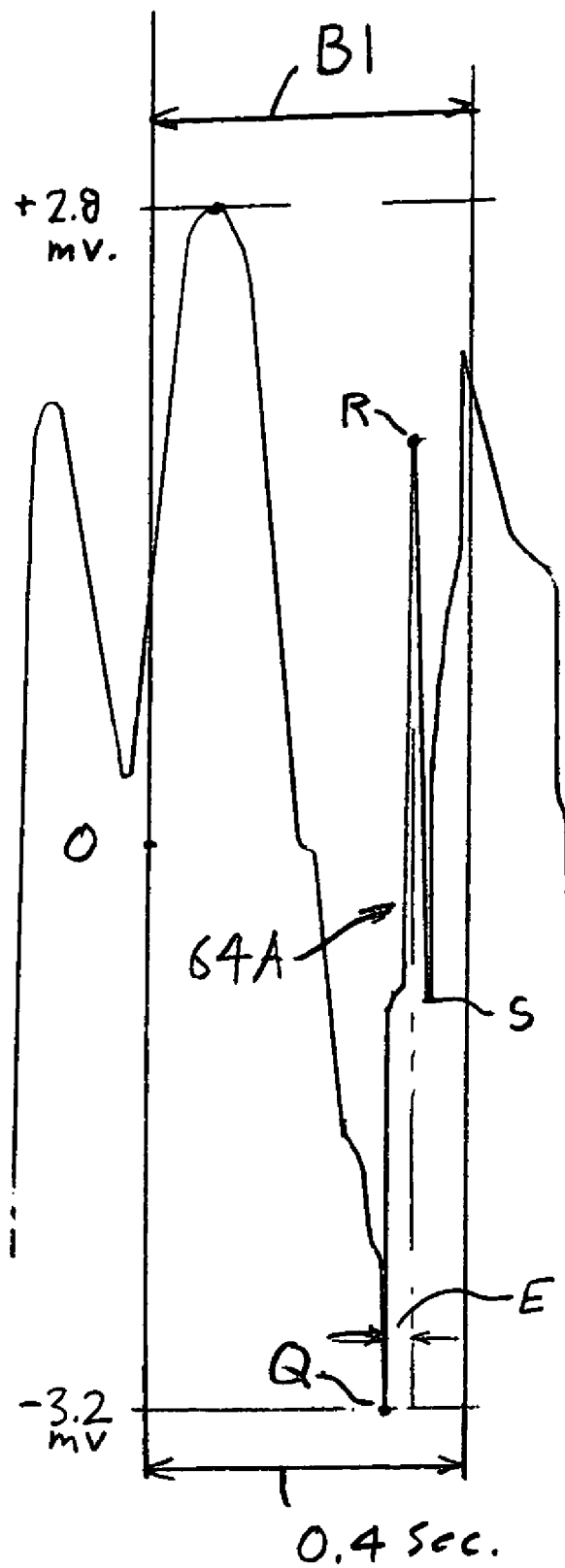
FIG. 6. Is an enlarged portion of the graph of FIG. 4, taken at location 64A thereof.

Another approach is to look for large changes in signal amplitude over short periods of time. In FIG. 4, the average of maximum changes in each cycle is a change F of about 10 mv during a compression artifact. In FIG. 6, which represents ECG signal portion B1 at 64A of FIG. 4, the signal between points Q and R has a voltage that rapidly increases. The increase is from −3.2 mv to +1.8 mv during a period E of about 0.05 second for a slope (derivative) of +100 mv/sec. This is followed by a voltage decrease from R to S of 1.8 mv during a period of about 0.03 second for a slope of −60 mv/sec. A slope of at least on the order of magnitude of 30 mv/sec (absolute value) between points differing in amplitude by at least about 10% of the changes in amplitude at the compression artifacts, indicates a portion of a QRS complex. The presence of two successive opposite slopes of the above magnitude is a much stronger indication of a QRS complex. In FIG. 6, each change from Q to R and from R to S is more than 10% of the change F (FIG. 4) in the compression artifact. This indicates a QRS complex. In the periods B2 of FIG. 5 there are no changes of more than 10% of the change G produced by the compression artifact.

The detection of QRS complexes can be confirmed by the fact that a detection of a signal portion that is part of a QRS complex, should constantly change phase with respect to the chest compression artifact in each cycle (which is the period between the middles, or peaks of two successive chest compression artifacts). Thus, the QRS complex will regularly occur almost simultaneously with the chest compression artifacts when the QRS complex cannot be detected, then QRS complexes will occur between artifacts and can be detected, and so forth. It is possible to set the frequency of chest compressions so they are close to expected heart beat cycles so a series of successive QRS complexes can be detected between chest compression.

It is possible to analyze the ECG signals 60, 70 (FIGS. 4 and 5) in regions that include periods A1, B1 that contain the chest compression artifacts 62, 82. However, it can be difficult to make such an analysis due to the high amplitude of the artifacts. One way is to obtain the profile of very regular chest compression artifacts (especially when a chest compressing machine is used) and cancel them in the ECG signal with signals that are 180° out of phase.

Thus, the invention provides a method for analyzing ECG signals from a patient who is receiving chest compressions, without the need for a extended interruption to provide "clean" ECG signals for detecting the heart rhythm and determining the need for an electrical shock. A possible exception is a hiatus that is a short period of time of a few seconds (perhaps 3 seconds but no more than 5 seconds) if the rescuer is not isolated from the patient's chest by an insulating sheet or is applying mouth-to-mouth resuscitation. The ECG signal which includes chest compression artifacts, is analyzed to determine the presence of a perfusing rhythm or of VF, in the presence of the compression artifacts. The analysis can continue without interruption (except possibly when a defibrillation pulse is applied). Compression artifacts are not removed but rather the QRS presence is identified in spite of the contamination of the signal by artifacts caused by chest compression. The method can include analyzing ECG signal portions lying between successive compression artifacts. In that method, applicant relies upon the constant phase shift between chest compressions and any heart beats, to provide QRS complexes that lie about halfway (e.g. between 25% and 75% of the time period between successive artifacts) between successive compression artifacts in about half of the cycles. These halfway signal portions can be isolated and analyzed apart from the rest of the ECG signal.

The method can include analyzing the corrupted ECG signal by producing a transform such as a Wavelet Transform. Then a group of spike regions thereof are selected that include high amplitude peaks and signals immediately adjacent to each peak. The autocorrelation of the group of spike regions is compared to crosscorrelations of the group of spike regions. Signals representing "white" areas between the autocorrelation and each crosscorrelation are produced to determine whether the ECG signal represents QRS complexes or a VF condition. In practice, two or more methods can be applied to analyze the ECG signal and they can all be used to judge whether or not a defibrillating shock should be applied. It is also possible to auto-correlate the average (e.g. 109 in FIG. 9) and to cross correlate that average with the group of spike regions that make up the average.

The novel features of the invention are set forth with particularity in the appended claims. The invention will be best understood from the following description when read in conjunction with the accompanying drawings.

What is claimed is:

1. A method for determining a treatment of a victim of possible cardiac arrest, while chest compressions are applied to the victim and ECG (electrocardiogram) signals of the victim are monitored to determine whether or not the heart generates QRS rhythms and whether or not the heart signals indicate ventricular fibrillation, comprising:

continuing to apply chest compressions to the victim while generating corrupted ECG signals that are corrupted by chest compression artifacts;

analyzing the corrupted ECG signals that are corrupted by chest compression artifacts to determine whether or not a defibrillating shock should be applied to the victim;

said step of analyzing the corrupted ECG signals includes producing first calculations representing an autocorrelation of each of a plurality of spike regions of a transform of the ECG signal and producing second calculations representing a crosscorrelation of said plurality of spike regions, calculating an integral of a magnitude of differences between said crosscorrelation and said autocorrelations and determining from said calculations whether or not the heart generates QRS rhythms or whether or not the signals indicate ventricular fibrillation.

2. A method for determining a treatment of a victim of possible cardiac arrest while chest compressions are applied to the victim and ECG (electrocardiogram) signals of the victim are monitored to determine whether or not a defibrillator shock should be applied to the victim, comprising:

continuing to apply chest compressions to the victim while generating corrupted ECG signals that are corrupted by chest compression artifacts;

analyzing the corrupted ECG signals that are corrupted by chest compression artifacts to determine whether or not a defibrillating shock should be applied to the victim;

said step of analyzing the corrupted ECG signals includes producing first calculations representing an autocorrelation of an average of a plurality of spike regions of a transform of the ECG signal and producing second calculations representing a crosscorrelation of said plurality of spike regions, and calculating an integral of a magnitude of differences between said crosscorrelation and said autocorrelations, and determining whether or not to deliver a defibrillating shock based on the amplitudes of said integrals.

3. Apparatus for use with electrodes that detect ECG signals taken from a victim, to indicate whether or not the ECG signals are from a heart with QRS rhythms, comprising:

means for generating an integral signal, wherein said means for generating performs a computation of a transform of said ECG signals, a computation of an autocorrelation of a group of spike regions of the transform, a computation of crosscorrelations of the group of spike regions, and a computation of integrals of the differences between each crosscorrelation and said autocorrelation;

means for indicating that the ECG signal is from a beating heart with perfusion rhythm when said integral signal is less than a predetermined value.

* * * * *